United States Patent [19]

Grossi et al.

[11] Patent Number: 5,151,101
[45] Date of Patent: Sep. 29, 1992

[54] SYSTEM FOR DISCONNECTABLY MOUNTING AN ENDOSCOPE SHEATH WITH AN ENDOSCOPE TOOL

[75] Inventors: Benedetto Grossi, Stamford, Conn.; Richard P. Muller, Bronx, N.Y.

[73] Assignee: Circon Corporation, Santa Barbara, Calif.

[21] Appl. No.: 615,461

[22] Filed: Nov. 19, 1990

Related U.S. Application Data

[62] Division of Ser. No. 513,550, Apr. 24, 1990, which is a division of Ser. No. 203,152, Jun. 2, 1988, Pat. No. 4,920,961.

[51] Int. Cl.⁵ .............................................. A61B 17/32
[52] U.S. Cl. ...................................................... 606/46
[58] Field of Search ..................... 128/4; 606/41, 46

[56] References Cited

U.S. PATENT DOCUMENTS

| 2,888,017 | 5/1959 | Wallace | 606/46 |
| 3,144,020 | 8/1964 | Zingale | 606/46 |
| 3,294,085 | 12/1966 | Wallace | 606/46 |
| 3,939,839 | 2/1976 | Curtiss | 606/46 |
| 3,939,840 | 2/1976 | Storz | 606/46 |
| 4,149,538 | 4/1979 | Mrava et al. | 606/46 |
| 4,423,727 | 1/1984 | Widran et al. | 606/46 |

Primary Examiner—Max Hindenburg
Attorney, Agent, or Firm—Daniel J. Meaney, Jr.

[57] ABSTRACT

A sheath is provided having a tube and a latch receptacle for removably connecting the sheath with a cooperating working element. The latch receptacle is static and has means for receiving at least a portion of a movable latch of the working element such that the latch receptacle can be disconnected from the working element without touching the sheath. A continuous flow resectoscope sheath assembly may also be provided with both an inlet post and an outlet post on the outer sheath portion.

10 Claims, 4 Drawing Sheets

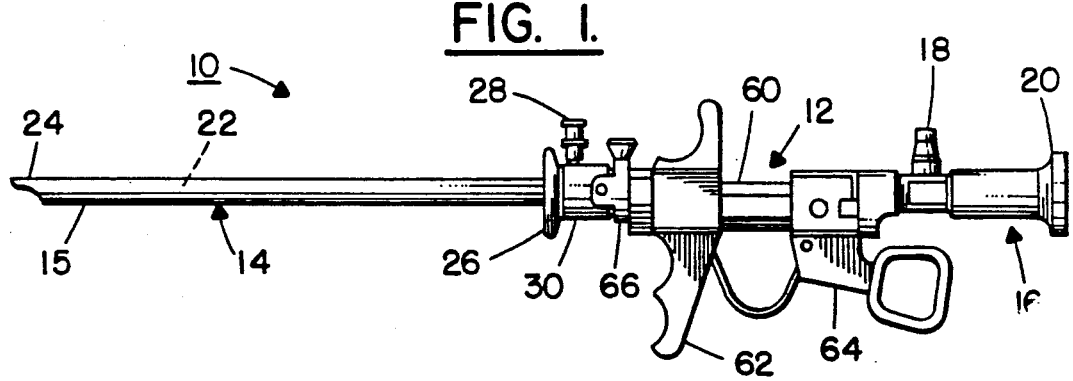
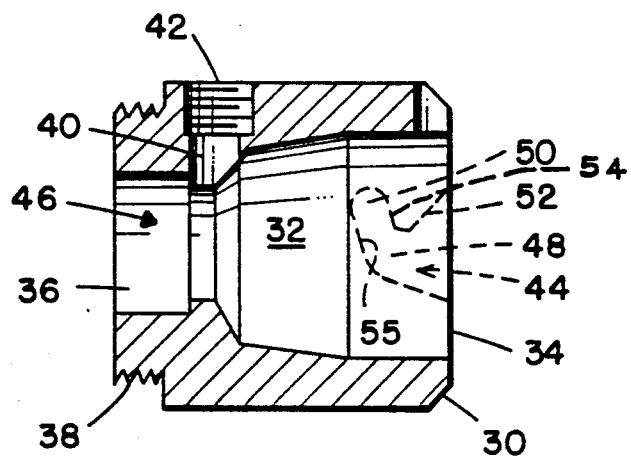
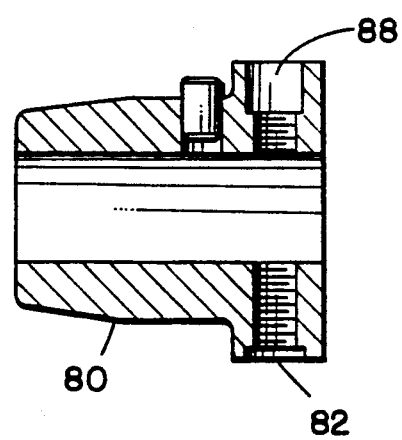
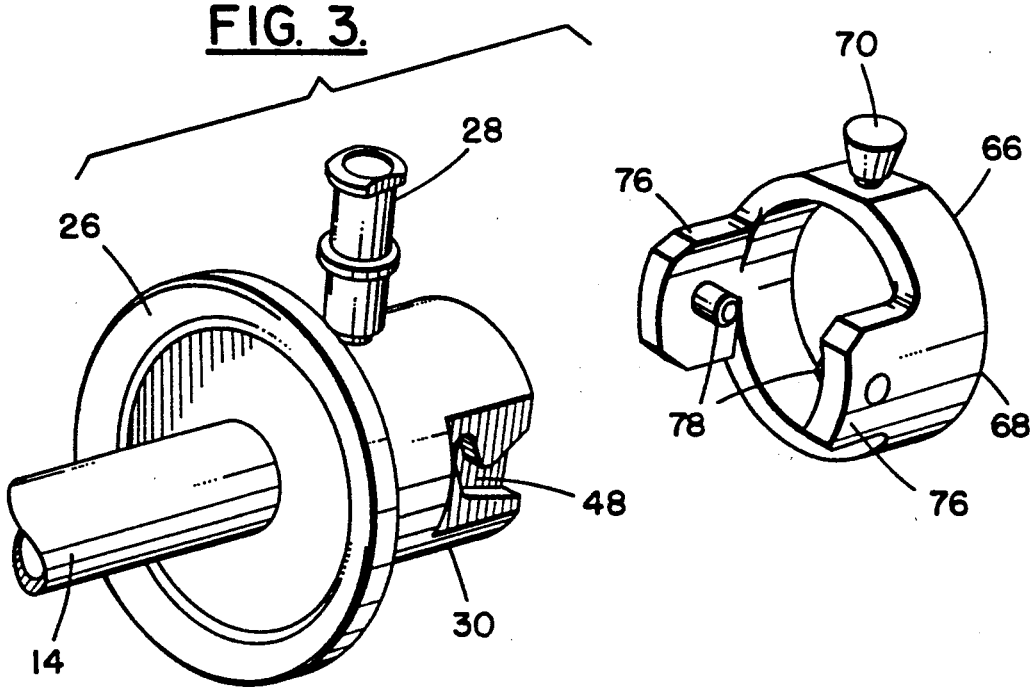

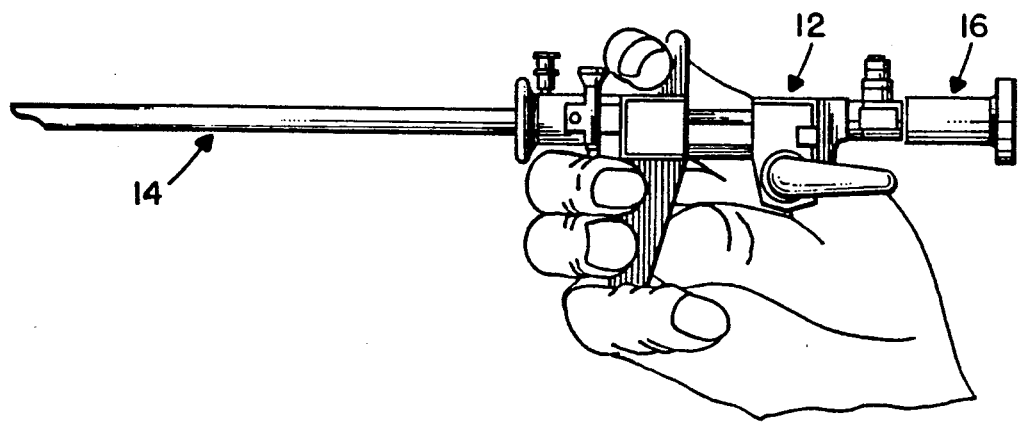
FIG. 4.
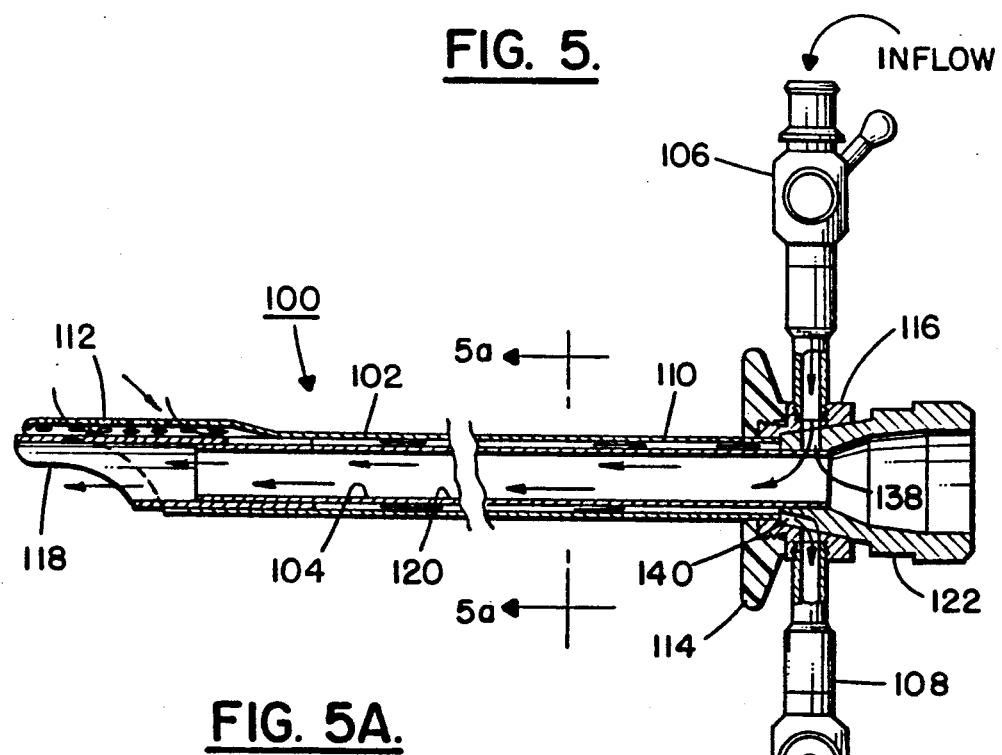
FIG. 5.
FIG. 5A.

SYSTEM FOR DISCONNECTABLY MOUNTING AN ENDOSCOPE SHEATH WITH AN ENDOSCOPE TOOL

This application is a division of Ser. No. 07/513,550 filed Apr. 24, 1990, pending, which is a division of Ser. No. 07/203,152 filed Jun. 2, 1988, now U.S. Pat. No. 4,920,961.

BACKGROUND OF THE INVENTION

1. Field of the Invention

This invention relates to medical endoscopes and, more particularly, to a system for disconnectably mounting a sheath with an endoscope tool.

2. Prior Art

Medical endoscopes and, in particular, resectoscopes having removable sheaths have been known and used for a number of years. The sheaths are generally made removable such that they can be used with different tools such as an obturator for insertion of the sheath into a human bladder, or a working element for presenting a telescope and an electrode to a target area, or an evacuator for washing the bladder; the sheath being capable of remaining in place while the different tools are changed.

Various different types of mounting connections between sheaths and tools such as working elements have been used in the past. U.S. Pat. No. 4,149,538 shows a latch mechanism on a sheath where, by depressing a button, the entire collar is shifted downward to permit stationary pins on the working element to be released from slots in the collar. U.S. Pat. No. 4,538,610 shows an axially rotatable connecting part provided on the resectoscope sheath. Circon ACMI of Stamford, Conn. has made and sold sheaths having a pivoting latch that cooperates with a fixed pin on various tools. Storz of West Germany, has also made and sold a resectoscope, Model 27040EJ, with an axially rotatable connecting part provided on the working element, but which required two hands to actively disconnect the sheath from the working element.

However, endoscopes of the prior art and, more particularly, resectoscopes, have not provided a simple and quick disconnect system between a sheath and a tool, such as a working element, which can be used with only one hand while still holding the working element with the same hand.

A further problem has arisen in the prior art in that sheaths with a movable latching or connecting mechanism are relatively expensive to manufacture and do not lend themselves to being disposable. Thus if the sheath is to be disposed of, the cost for replacement is relatively expensive.

It is therefore an objective of the present invention to provide a sheath for use with an endoscope having a simple static latch receptacle that allows for disconnecting the sheath from a tool without touching the sheath.

It is also an objective of the present invention to provide a sheath for use with an endoscope having a simple static latch receptacle that is economically manufactured such that it is disposable and replaceable at a reasonable cost.

It is a further objective of the present invention to provide a tool for use in resectoscopy having a connector that can connect the tool to a cooperating sheath and allow for removal of the tool from the sheath without touching the sheath.

It is a further objective of the present invention to provide a new and improved continuous flow irrigation sheath.

SUMMARY OF THE INVENTION

The foregoing problems are overcome and other advantages are provided by a system for disconnectably mounting an endoscope sheath with an endoscope tool.

In accordance with one embodiment of the invention, a sheath is provided for use with an endoscope. The sheath generally comprises a tube means and a latch receptacle means for removably connecting the sheath with a cooperating tool. The latch receptacle means is static and has means for receiving at least a portion of a movable latch means of the tool therewith whereby the latch receptacle means can be disconnected from the tool without the user touching the sheath.

In accordance with another embodiment of the invention, a tool for use in resectoscopy is provided generally comprising a frame means and means for removably connecting the tool with a cooperating sheath. The connecting means comprises a movable latch means having at least one latch receivable in a static latch receptacle of the sheath. The latch means has a biasing means for biasing the latch in a first position for retaining the sheath, but movable to a second position for disconnecting the sheath whereby the tool is removable from the sheath without an operator touching the sheath.

In accordance with another embodiment of the invention, a urological endoscope is provided comprising a sheath means; a tool means; and means for releasably connecting the sheath means with the tool means. The connecting means comprises a movable latch means on the tool means and a latch receptacle means on the sheath means. The latch means comprises a biasing means and at least one latch pin biased in a first position, but movable to a second position when connecting and disconnecting the sheath means. The latch receptacle means comprises at least one notch for receiving said at least one latch pin. The notch has a first surface for moving the latch pin from the first position as the sheath means and tool means are being connected and a second surface for cooperating with the biasing means to retain the latch pin in the notch whereby the latch means can be moved to remove the sheath means.

In accordance with another embodiment of the invention, a urological endoscope sheath is provided comprising an outer tube means and an inner tube means. The outer tube means has an irrigation inlet post and a turbid fluid outlet post extending from a proximal end of the outer tube means. The posts communicate with an inner conduit of the outer tube means. The inner tube means is removably mountable with the outer tube means and has an irrigant inlet passage alignable with the inlet post such that irrigant entering the sheath can pass into the inner tube means and move towards a target area. Turbid fluid can be removed through a space between the outer tube means and the inner tube means and exited through the outer post. The space is closed at the proximal end of the sheath and the inner tube means has a proximal tip being substantially sealable by the thumb of an operator whereby a working element can be removed from the sheath while allowing substantially continuous inflow of irrigant towards a target area.

BRIEF DESCRIPTION OF THE DRAWINGS

The foregoing aspects and other features of the invention are explained in the following description, taken in connection with the accompanying drawings wherein:

FIG. 1 is a side view of a resectoscope incorporating features of the invention.

FIG. 2A is a cross-sectional side view of a connector portion of a sheath.

FIG. 2B is a cross-sectional side view of a cone connector of an endoscope tool.

FIG. 3 is an exploded perspective view of the connector portion of sheath and the movable latch assembly of an endoscope tool.

FIG. 4 is a side view of a resectoscope being held by an operator.

FIG. 5 is a partial cross-sectional view of a continous flow resectoscope sheath.

FIG. 5A is a cross-sectional view of the sheath shown in FIG. 5 taken across lines 5A—5A.

DETAILED DESCRIPTION OF THE INVENTION

Figure 3A:
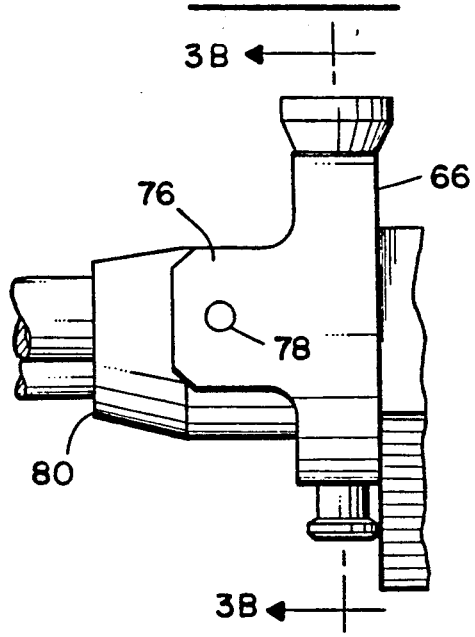
FIG. 3A is a side view of a connector portion of a resectoscope working element.

Referring to FIG. 1, there is shown one embodiment of a resectoscope 10 incorporating features of the present invention. Although the present invention will be described with reference to resectoscopes it should be understood that the present invention can be used with any endoscope comprising a sheath and a tool. In addition, any suitable size, shape or type of material can be used in the elements of the present invention. Cross-reference is hereby made to the following co-pending patent applications; "Improved Resectoscope Electrode and Method For Making The Same" by Grossi et al., Ser. No. 07/202,153, filed Jun. 2, 1988; "Resectoscope With Improved Guide Block And Electrical Plug Connection" by Grossi et al., Ser. No. 07/202,154, filed Jun. 2, 1988; "System For Reducing Drag On The Movement of An Electrode In A Resectoscope And Method Of Making The Same" by Grossi et al., Ser. No. 07/201,667, filed Jun. 2, 1988; Design For A "Resectoscope Electrode", by Grossi et al., Ser. No. 07/201,667, filed Jun. 2, 1988; Design For A "Resectoscope Handle And Latch" by Grossi et al., Ser. No. 07/203,021, filed Jun. 2, 1988; and Design For A "Resectoscope Sheath Latch Receptacle" by O'Hare et al., Ser. No. 07/201,711, filed Jun. 2, 1988 assigned to the same assignee as herein and which are incorporated by reference in their entirety herein.

In the embodiments shown in FIG. 1, the resectoscope 10 generally comprises four main parts; a working element 12, a sheath 14, a telescope 16 and an electrode assembly (not shown). The telescope 16 is removably mounted to the working element 12 and has a connector 18 for connecting fiber optics of the telescope 16 with a light source (not shown) via a optical connector (not shown). A bundle or bundles of light transmitting fibers in the telescope 16 can transmit light from the connector 18 to a distal end of the telescope 16 to illuminate a target area. An image of the target area can be transmitted back to an eyepiece 20 of the telescope 16 for viewing by an operator.

The sheath 14, in this embodiment, can generally be described as a rigid tube intended for insertion through the urethra of a patient. The sheath 14 has a tube 15 with a channel 22 for passage of portions of the working element 12, telescopes 16 and electrode assembly (not shown) therethrough. The sheath 14 generally has an open distal end 24 that can be positioned in the patient's bladder and provides the electrode assembly with an opening such that the electrode assembly can be advanced past the sheath distal end 24 to perform a desired operation and such that the telescope 16 is provided with an operative field of view. In this embodiment, the distal end 24 of the sheath 14 has a shaped fenestra configuration. The tube portion 15 of the sheath 14 can be made of any suitable material. However, in a preferred embodiment, the tube portion 15 of the sheath 14 is comprised of a polymer or plastic material that allows for convenient disposal. The sheath 14, in this embodiment, has a proximal end comprising a meatus shield 26, an irrigation post 28 and a connector 30.

Referring to FIG. 2a, a cross sectional side view of the connector 30 is shown. The connector 30 can be made of any suitable material. However, in a preferred embodiment the connector 30 is comprised of metal. However, any suitable material can be used including non-metallic material. The connector 30 has a generally circular outer perimeter with a patterned channel 32 passing therethrough from a first end 34 to a second end 36. Threads 38 are provided proximate the second end 36 for mounting the meatus shield 26 to the connector 30. However, any suitable mounting means could be used to mount the meatus shield 26 to the sheath 14 or alternatively no meatus shield 26 need be provided. Radially extending into the center channel 32 is a port 40 having threads 42 for mounting the irrigation post 28 to the connector 30. However, any suitable means could be used to mount the post 28 to the sheath 14. Referring now to the center channel 32, the channel has a first portion 44 and a second portion 46. The first portion 44 of the channel 32 can generally be described as cone shaped and is intended to receive a suitable coned shaped member of a tool being used with the sheath 14 and make a sealing engagement therewith. The second portion 46 of the channel 32 is suitably sized and shaped to receive a proximal end of the sheath tube 15 such that the sheath tube 15 and connector 30 are fixedly mounted to each other therearound. In this embodiment, the connector 30 comprises two laterally disposed slots or notches 48 that act as latch receptacles for receiving latches on a tool being used with the sheath 14 to connect the sheath 14 with the tool being used therewith. Although the slots 48 are shown in FIG. 2A as blind slots wherein they do not pass entirely through the connector 30 but merely form exterior notches on the outer perimeter of the connector 30, in an alternate embodiment, the slots 40 may be provided as passing entirely through the connector 30 from the outer perimeter to the inner channel 32.

The shape of the notches 48 generally serve three functions. The first function is to properly allow entry of a latch pin on a tool being mounted with the sheath 14 into an inner portion 50 of the notches 48. The second function is to retain these latch pins in the notches 48. The third function is to cause an axial release and ejection of the sheath from the endoscope tool when the movable latching assembly is activated at a connected position. To perform these functions the notches 48 comprise a first surface 52 proximate the first end 34 of the connector, a second surface 54 located in the inner portion 50 of the notches 48, and a third surface 55 also in the inner portion 50 of notches 48. The first surface 52 is generally provided to channelize the latch pins of the tool being connected with the sheath 14 into an area proximate the inner portion 50. Once the latch pins have been positioned in the inner portions 50, the second surface 54 provides the function of substantially preventing the latch pins from being removed from the inner portion 50 and effecting a substantially watertight connection between the sheath and the endoscope tool as will be described in more detail below.

Referring back to FIG. 1, the working element 12 generally comprises a frame 60, a handle 62, a movable guide block 64, a movable latch assembly 66 and extending telescope and electrode assembly sleeves (not shown). The working element 12, shown in this embodiment, is generally known as an Iglesias type working element. However, other types of working elements, such as a McCarthy type working element, may also be provided with features of the present invention. The working element 12, as is generally known in the art, serves as a means for connecting electrosurgical current from an electrosurgical generator (not shown) to the electrode. The working element 12 also provides a means for the operator to control the resectoscope and is capable of slidingly moving the electrode axially, such axial movement being observable through the eyepiece 20 of the telescope 16.

Figure 3B:
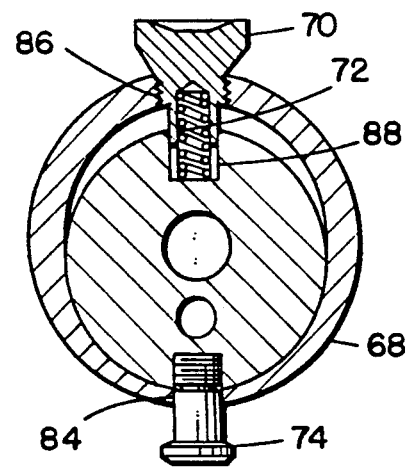
FIG. 3B is a cross-sectional view of the connector portion shown in FIG. 3A taken across lines 3B—3B.

Referring now to FIGS. 3A and 3B a partial side view of the movable latch assembly portion of the working element 12 and a cross sectional view of the movable latch assembly 66 is shown, respectively. The movable latch assembly 66, in this embodiment, generally comprises a movable ring 68, a control button 70, a spring 72, a stabilizing pin 74, two forwardly extending arms 76 and two latch pins 78. The movable latch assembly 66 is attached to the frame 60 of the working element 12 proximate a cone connector 80. The cone connector 80 can be made of any suitable material. However, in this embodiment, the cone connector 80 is made of metal. The cone connector 80 is generally cone shaped and suitably sized and shaped to be matingly inserted into the first portion 44 of channel 32 of the connector 30 and form a substantial seal therewith. The movable ring 68 is slightly larger than the proximal end of the cone connector 80 and is mounted therearound. The stabilizing pin 74 is fixedly connected to a first aperture 82 at the bottom proximal end of the cone connector 80 and passes through a pin aperture 84 in the movable ring 68 with a slidable fit therebetween. The top portion of the movable ring 68 also has a button aperture 86 with the control button 70 fixedly mounted therein. The control button 70 has a portion that extends inwardly towards the cone connector 80 with the spring 72 being slightly compressed between a seat in the button 70 and a button spring seat 88 on the proximal top end of the cone connector 80. Thus assembled, the movable ring 68 and arms 76 with integrally attached latch pins 78 are movable relative to the cone connector 80 in an up and down reciprocation. In this embodiment, the spring 72 acts to bias the movable ring 68 in a direction to engage surface 54 of inner portions 50 in an upward first position. However, an operator, by depressing the control button 70, can further compress the spring 72 and move the ring 68 downward with the pin aperture 84 of the ring 68 sliding along the stabilizing pin 74 until a second position is reached. The latch pins 78 can contact the third surface 55 such that the surface 55 and pins 78 push the working element 12 and sheath 14 apart.

Referring now also to FIG. 3 an exploded perspective view of the sheath connector 30 and the movable latch assembly 66 is shown. As can be seen, the latch pins 78 and arms 76 are orientated such that the pins 78 can be received in the slots 48 which act as latch receptacles with the pins 78 acting as latches for fixedly, but removably connecting the sheath 14 with the working element 12. The working element 12 is generally inserted to the sheath 14 by passing the telescope and electrode assembly sleeves through the first portion 44 of the channel 32 and into the tube 15 of the sheath. As the working element 12 is advanced into the sheath 14 the cone connector 80 is inserted into the first portion of the channel 32. The arms 76 of the ring 68 start to pass along the outside of the connector 30 and the latch pins 78, being biased in the upper first position, come into contact with the first surface 52 of the connector 30. With the further insertion of the working element 12 into the sheath 14 the sloped surface of the first surface 52 forces the latch pins 78 downward thereby moving the ring 68 downward and compressing the spring 72. With the further insertion of the working element 12 into the sheath 14 the tapered or cone shaped surface of the cone connector 80 comes into contact with the tapered or cone shaped aperture of the first portion 44 of the channel 32 in the connector 30. The latch pins 78, having been pushed downward by the sloped surface of the first surface 52 can move into the inner portions 50 of the slots 48. As the pins 78 move into the inner portions of the slots 48, the spring 72 in the latch assembly 66 biases the latch assembly 66 upward and the pins 78 travel along the sloped surface of the second surface 54 in the slots 48 and are retained therein. Because the second surfaces 54 are slightly sloped in a forward direction the pins 78 and thus the cone connector 80 are biased in a forward direction such that the tapered shape of the cone connector 80 is biased against the tapered cone shape of the first portion of channel 32 and thus substantially seals the two members together. In addition, because the latch pins 78 are biased in an upward direction and are contained in the inner portions 50 having only a downward entrance or exit, the sheath 14 and working element 12 can only be separated by an operator depressing the control button 70 to move the latch pins 78 downward and then withdrawing the working element 12 from the sheath 14.

Figure 6:
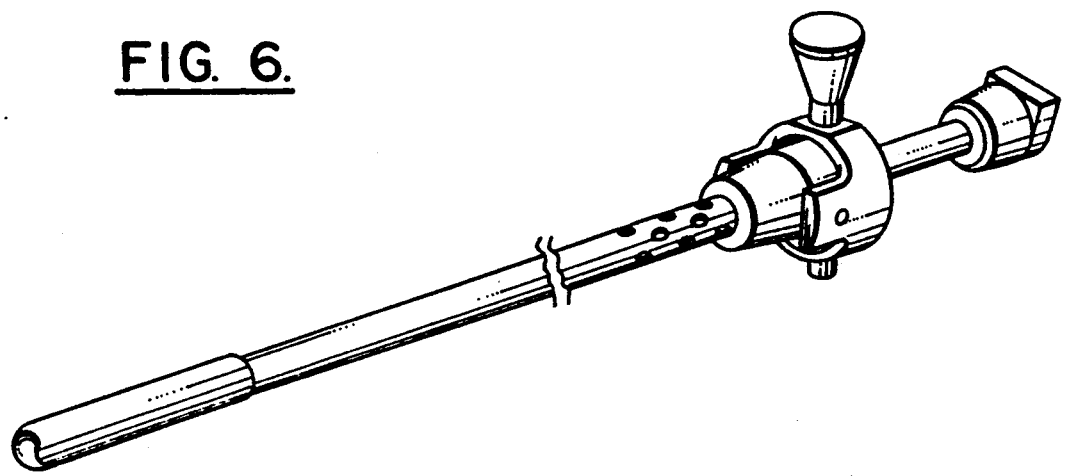
FIG. 6 is a perspective view of a obturator comprising features of the invention.
Figure 7:
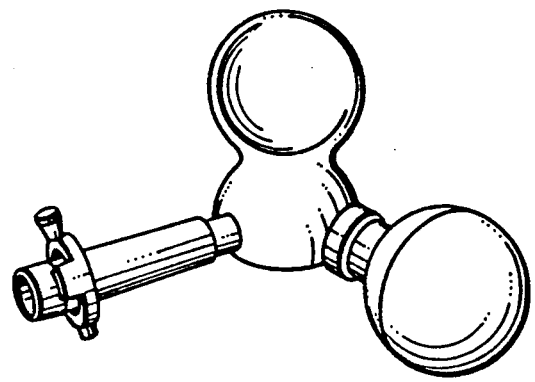
FIG. 7 is a perspective view of an evacuator comprising features of the invention.

Referring now to FIG. 4, a principle feature or advantage of the invention will be described. FIG. 4 is a side view of a McCarthy type resectoscope being held in the right hand of an operator. As shown, an operator generally grasps the resectoscope on the handle 62 with at least one finger on the upper portion of the handle. The present invention allows for the operator to disconnect the working element 12 from the sheath 14 for minimal delay of the operative procedure. It also allows for disconnection without the operator actually having to touch the sheath 14. One of the principal features of the present invention is the quick release aspect of the disconnectability. Unlike other instruments, the present invention allows for convenient disconnection of the sheath from a tool by the use of only one hand; the same hand operating or holding the tool. The operator does not necessarily have to use his second hand to cause disconnection as with sheathes having movable latch receptacles. In addition, this advantage of the present invention is particularly useful when the operator has removed the sheath 14 from the patient and desires to disconnect the sheath 14 from the working element 12 without having to touch the sheath 14 because of biological waste and contaminates on the sheath 14. This is particularly advantageous when disposing of the sheath 14. The operator need only tilt the resectoscope such that the sheath 14 is in a downward position over a trash receptacle and by moving his finger on the top of the handle 62 to the control button 70 and moving the top finger to depress the movable ring 68, the latch pins 78 being moved therewith, the sheath 16 will merely slide off of the working element 12 do to gravity. Another clearly advantageous feature of the present invention is the decreased cost of manufacture for a sheath having features of the present invention. The presently available sheaths in the art generally comprise a movable latch receptacle that cooperates with stationary latches on the working element. However, because of the movable aspect of the latch receptacles the sheaths presently available in the art are relatively expensive and do not lend themselves to being disposable. Another principal advantage of the present invention is the fact that the latch receptacles on the sheath are static and are relatively easy to manufacture thus reducing the cost of a sheath and allowing for a safer and more convenient medical atmosphere. In addition to resectoscopes, the present invention can be used with any tool. As shown in FIG. 6, the present invention can be used with an obturator; timberlake or visual. As shown in FIG. 7 the present invention can be used with an evacuator.

The present invention can be used with a rotatable irrigation post on the sheath. The present invention may also be used with a continuous flow resectoscope as shown in FIG. 5.

Referring now to FIG. 5, a partial cross sectional sideview of a continuous flow resectoscope sheath assembly 100 is shown. The sheath assembly 100 generally comprises an outer sheath 102 and an inner sheath 104. The outer sheath 102 generally comprises a tube 110, an aperture distal end 112 and a proximal end having a meatus shield 114, an inner sheath connector portion 116, an irrigation inlet 106 and a turbid fluid outlet 108 connected thereto. The inner sheath 104 generally fits within the outer sheath 102 and generally comprises an insulated distal end 118, a tube portion 120 and a connector portion 122. The outer sheath 102 and inner sheath 104 are mounted to each other such that a space 124, as shown in FIG. 5A, exists between the outer perimeter of the inner sheath 104 and the inner perimeter of the outer sheath 102.

Figure 5B:
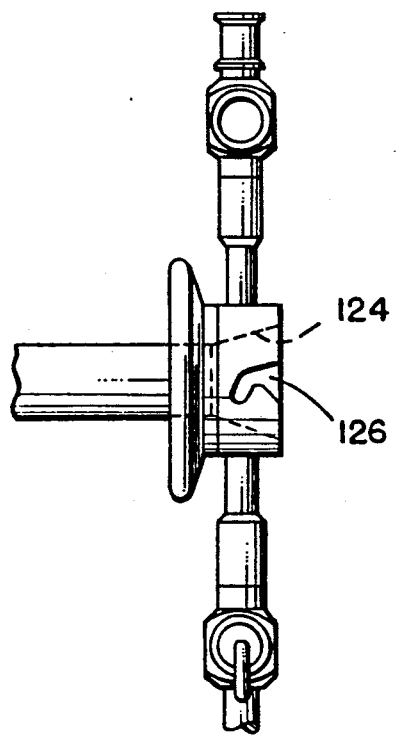
FIG. 5B is a side view of the proximal end of the outer sheath of the continuous flow sheath shown in FIG. 5.
Figure 5C:
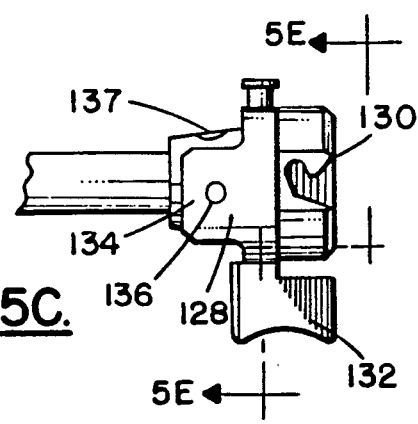
FIG. 5C is a side view of the proximal end of the inner sheath of the continuous flow sheath shown in FIG. 5.
Figure 5E:
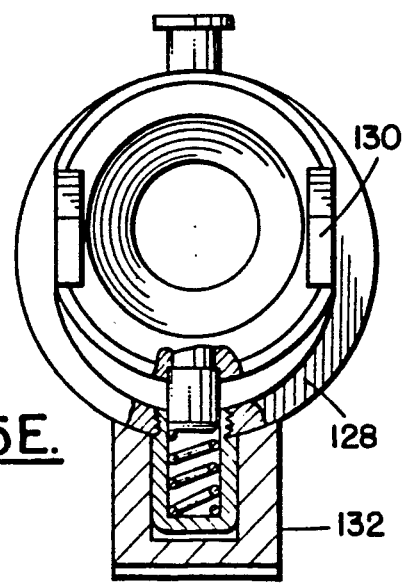
FIG. 5E is a cross-sectional view of the proximal end of the inner sheath taken across lines 5E—5E of FIG. 5C.
Figure 5D:
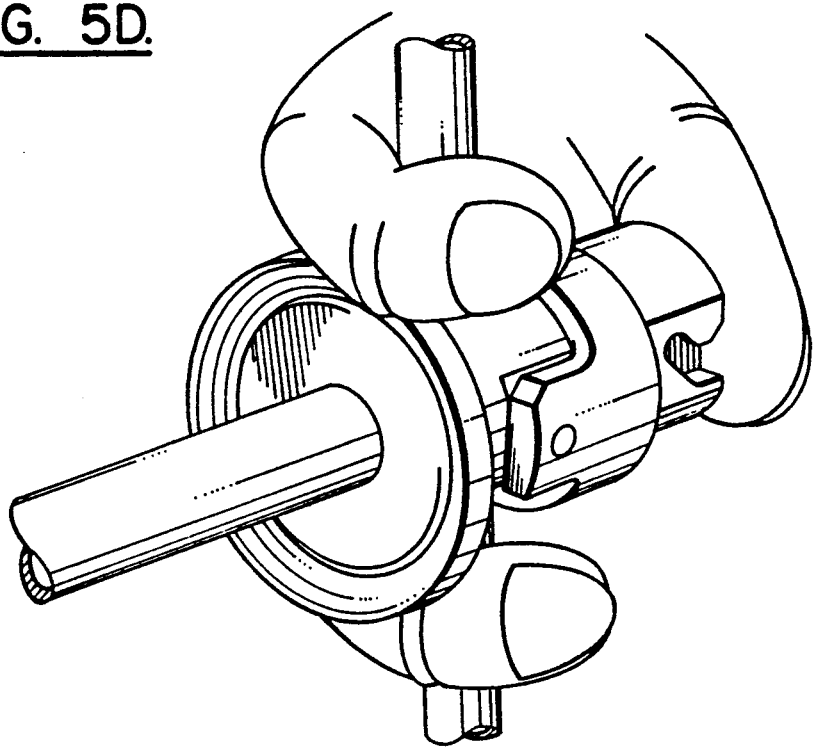
FIG. 5D is a perspective view of an operator's hand temporarily sealing off the proximal end of a sheath with his thumb.

FIGS. 5B and C show a side view of the proximal end of the outer sheath 102 and a side view of the proximal end of the inner sheath 104, respectively. The connector portion 116 of the outer sheath 102 generally comprises a cone shaped aperture 124 and two laterally disposed notches 126. In this embodiment the notches 126 are orientated to receive a downwardly biased movable latch assembly 128 on the inner sheath 104. The connector portion 122 of the inner sheath 104 generally comprises both the movable latch assembly 128 for connection to the static latch receptacle on the outer sheath 102 and a static latch receptacle 130 for connection to a movable latch assembly on a resectoscope tool. In the embodiments shown in FIG. 5C and 5E, the movable latch assembly 128 is biased in a downward position and has a button 132 which an operator can move to move two arms 134 in an upward direction to insert or remove latch pins 136 from the notches 126 in the outer sheath 102. The static latch receptacles of the inner sheath 104 and outer sheath 102 are substantially identical to the latch receptacle described with reference to FIG. 2A. In this embodiment the latch receptacles are provided with blind slots such that an operator can substantially seal the proximal end of either the inner or outer tubes by placing a finger over a proximal end aperture as shown in FIG. 5D.

Referring to FIG. 5 the connector portion 122 of the inner sheath 104 generally comprises an inlet aperture 138 on its cone connector 139 that allows irrigant from the irrigation inlet 106 to enter into the center of the inner sheath 104. A channel 140 is located on the exterior of the cone connector 139 and allows turbid fluid to be withdrawn from the space 124 through the turbid fluid outlet 108. A principal advantage of the present invention is that an operator can withdraw a resectoscope working element from the sheath 100 and by covering the proximal aperture of the inner sheath 104 allow for the continuous inflow of irrigant to the target area thereby maintaining distention of the bladder. In addition, the operator may also remove the inner sheath 104 from the outer sheath 102, but nonetheless provide a continuous inflow of irrigant to the target area. This is particularly advantageous because when removing a working element from the sheath 100 irrigant that is in the bladder of a patient is lost through the sheath 100 before an operator can cover the proximal aperture to the sheath. Therefore, the continuous inflow of irrigant to the bladder replenishes the lost irrigant such that a more efficient evacuation procedure or the like can be performed.

It should be understood that the foregoing description is only illustrative of the invention. Various alternatives and modifications can be devised by those skilled in the art without departing from the invention. Accordingly, the present invention is intended to embrace all such alternatives, modifications and variations which fall within the scope of the appended claims.

What is claimed is:

1. A tool for use in resectoscopy comprising:
frame means defining a working element; and
means operatively connected to the frame means for removably connecting a cooperating sheath having a static latch receptacle means to said working element, said removably connecting means comprising a reciprocally movable latch means having at least one latch member, said reciprocally movable latch means having a biasing means for biasing said at least one latch member in a first position for retaining said at least one latch member within said static latch receptacle means removably connecting said cooperating sheath to said working element, but movable to a second position for disconnecting the at least one latch member from the static receptacle means wherein the static latch receptacle means cooperates with said at least one latch member to urge said working element away from the cooperating sheath whereby the working element is removable from the cooperating sheath without an operator touching the cooperating sheath.

2. A tool as in claim 1 wherein the frame means defining a working element is a frame means defining a resectoscope working element.

3. A tool as in claim 1 wherein the cooperating sheath is an obturator.

4. A tool as in claim 1 wherein the cooperating sheath is an evacuator.

5. A tool as in claim 1 wherein said reciprocally movable latch means has a depressible release button operatively coupled to the biasing means for moving said at least one latch member from said first position to said second position.

6. A tool as in claim 1 wherein said reciprocally movable latch means comprises a latch ring with at least one laterally disposed inwardly projecting latch pin for removing connecting said working element with said static latch receptacle means of the cooperating sheath in the first position and for disconnecting said working element from said static latch receptacle means of the cooperating sheath in the second position.

7. The tool as in claim 1 wherein the static latch receptacle means has at least one notch means for receiving and channelizing said at least one latch member of the reciprocally movable latch means, said reciprocably movable latch means being capable of linearly moving between the first position wherein said at least one latch member is retained in said at least one notch means and the second position wherein said at least one notch means cooperates with said at least one latch member to urge said working element away from said cooperating sheath whereby said static latch receptacle means can be disconnected from the working element without touching the cooperating sheath.

8. The tool as in claim 7 wherein the at least one notch means includes a surface for causing an axial release and ejection of the cooperative sheath from the working element when the reciprocally movable latch means is moved into the second position.

9. The tool as in claim 1 wherein said reciprocally moveable latch means has two latch members and wherein said static latch receptacle has two notches for receiving said two latch members.

10. The tool as in claim 9 wherein the two latch members are latch pins.

* * * * *